United States Patent [19]

Garner

[11] 4,285,232

[45] Aug. 25, 1981

[54] MONITOR ASSEMBLY FOR ELECTROCHEMICAL CORROSION PROTECTION OF STAINLESS STEEL BLEACH PLANT WASHERS

[75] Inventor: Andrew Garner, Pointe Claire, Canada

[73] Assignee: Pulp and Paper Research Institute of Canada, Pointe Claire, Canada

[21] Appl. No.: 132,026

[22] Filed: Mar. 20, 1980

[51] Int. Cl.³ ............................................. G01N 17/00
[52] U.S. Cl. .................................... 73/86; 204/195 C
[58] Field of Search .......................... 73/86; 23/230 C; 204/195 C; 422/12, 13, 53

[56] References Cited

U.S. PATENT DOCUMENTS

| 3,418,848 | 12/1968 | Schaschl | 73/86 |
| 3,649,492 | 3/1972 | Marsh et al. | 204/195 C |
| 4,181,882 | 1/1980 | Isaacs et al. | 204/195 C X |

*Primary Examiner*—James J. Gill
*Attorney, Agent, or Firm*—Lawrence I. Field

[57] ABSTRACT

A monitor assembly for monitoring the effectiveness of a method and apparatus for electrochemical crevice corrosion protection by electrochemical potential control of a stainless steel vessel containing a corrosive washing solution, e.g. bleach plant washer equipment used in the pulp industry.

16 Claims, 4 Drawing Figures

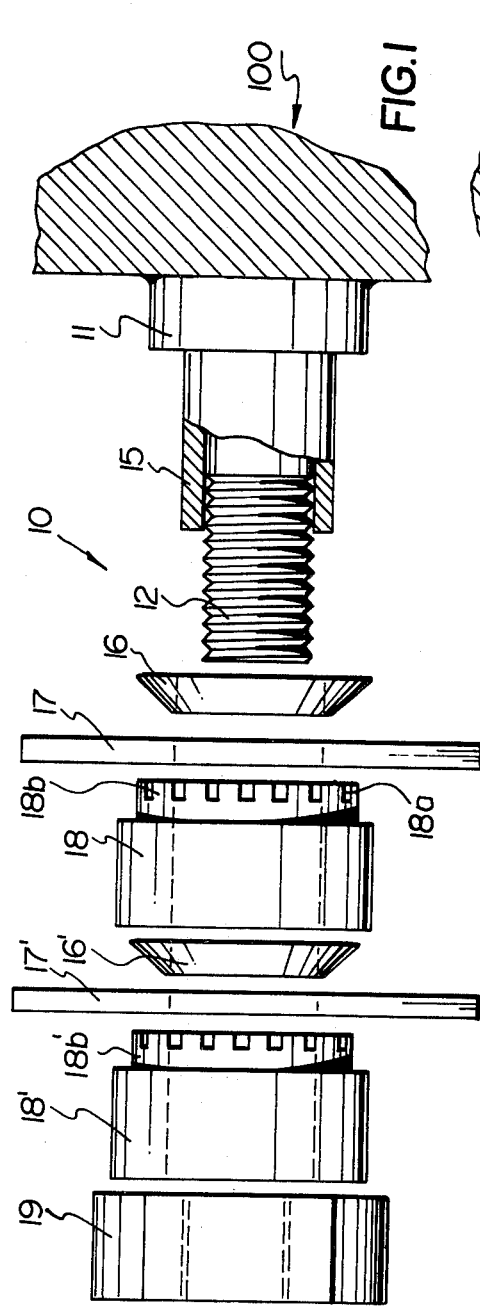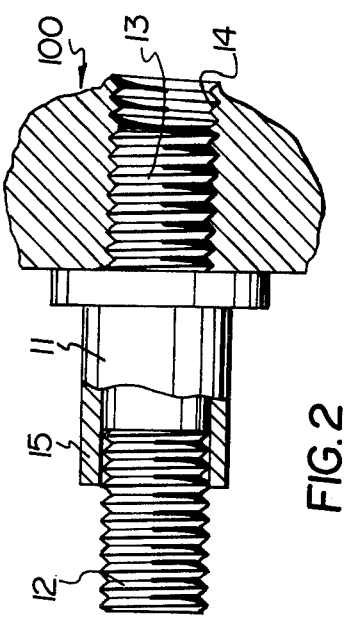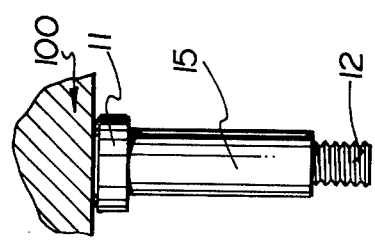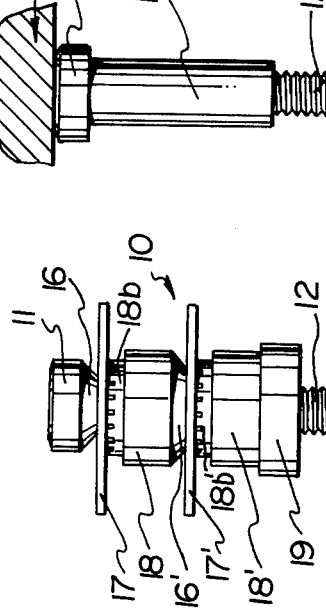

MONITOR ASSEMBLY FOR ELECTROCHEMICAL CORROSION PROTECTION OF STAINLESS STEEL BLEACH PLANT WASHERS

BACKGROUND OF THE INVENTION (i) Field of the Invention

This invention relates to a monitor assembly for monitoring a method and apparatus for corrosion protection by electrochemical potential control of a stainless steel vessel containing a corrosive washing solution. More particularly, it is directed to such a monitor assembly for use in a method and apparatus for protecting stainless steel bleach plant washer equipment, used in the pulp industry, from corrosion.

(ii) Description of the Prior Art

Stainless steel is known to be generally resistant to corrosion due to a build-up thereon of passive films. However, such passive films are susceptible to localized breakdown, and this susceptibility is greatly enhanced in the presence of specific ions. The filtrate used in a bleach plant washer generally contains oxidants, e.g., chlorine ($Cl_2$), chlorine dioxide ($ClO_2$), or hypochlorite ($OCl^-$), together with a considerable amount of chloride ions. Such filtrate can bring about localized passive film failure. The loss of protection leads to various modes of localized corrosion, the principal ones being crevice corrosion and pitting corrosion.

The corrosion environment in chlorine and chlorine dioxide stage bleach plant washers is generally acidic, with a pH in the range of 1 to 7. The most common alloys of construction are 316L and 317L stainless steel. In a number of cases, the corrosion of these washers has been so severe that the replacement washer was constructed from stainless steel with higher molybdenum content, at significantly higher cost.

One procedure heretofore used to control corrosion in such bleach plant washers was the addition of antichlors, e.g., $SO_2$ or NaOH. Such antichlors as used at present are intended to make the environmental conditions in the washer less oxidizing and so less corrosive to the stainless steel washer components. It has been found, however, that under typical chlorine dioxide washing stage conditions, for example, $SO_2$ additions alone will inhibit but will not substantially completely prevent crevice corrosion in many types of stainless steels.

The corrosive environment in hypochlorite stage bleach washers is generally alkaline, with a pH in the range of 8-11. The most common alloy of construction is 316L stainless steel. It would be preferable to use 304L stainless steel since it is much cheaper than 316L stainless steel. However, 304L stainless steel has been largely unsuccessful for this use because of severe chloride crevice corrosion.

Electrochemical corrosion control would seem to offer a solution to the widespread problem of crevice corrosion of stainless steel in bleach washing stages. Many patents teach the concept of corrosion control by inducing passivity in the metal by anodic polarization techniques. In such technique, the vessel to be protected against corrosion by a chemical contained therein is anodically polarized with respect to an inert electrode suspended in the corrosive liquid in the vessel. An electric current is then passed between the metallic vessel and the inert cathode so as to maintain the electrical potential of the vessel in the passive region. The necessary electrical potential can be determined by means of an anodic polarization curve, or by controlled potential immersion testing. The passive region can be identified after such tests, thus providing data indicative of the potential range within which the vessel should be maintained in order to attempt to minimize corrosion.

Amongst the prior patents dealing with this technique are: Banks et al., U.S. Pat. Nos. 3,371,023 issued Feb. 7, 1968, 3,375,183 issued Mar. 26, 1968, 3,378,472 issued Apr. 16, 1968, 3,379,629 issued Apr. 23, 1968, and 3,409,526 issued Nov. 5, 1968; Elmore et al., U.S. Pat. No. 1,576,581 issued Mar. 16, 1926; Hoey, U.S. Pat. No. 3,442,779 issued May 6, 1969; Poyser, U.S. Pat. No. 4,018,647 issued Apr. 19, 1977; and Hulthe, U.S. Pat. No. 4,036,716 issued July 19, 1977.

Cathodic polarization has also been applied in the past for the protection of metals that do not form passive films, e.g., iron in soil or sea water. It has been applied to stainless steels in neutral sea water solutions, but its application to stainless steels in strongly oxidizing solutions involves a number of possible difficulties, namely concerned with the problem of not destroying the passive film when the potential is lowered to a potential near or below the protection potential. Precise control of the impressed current in a cathodic system is thus a prime equipment.

Amongst the prior patents which relate to the application of cathodic polarization of metal surfaces including such precise control of the impressed current are: MacTaggart et al., U.S. Pat. No. 2,435,973 issued Feb. 17, 1948; Stephens, Jr., U.S. Pat. No. 3,634,222 issued Jan. 11, 1972; Kipps et al., U.S. Pat. No. 3,692,650 issued Sept. 19, 1972; and Ferry et al., U.S. Pat. No. 4,080,272 issued Mar. 21, 1978.

A major difficulty in electrochemical corrosion protection of stainless steel bleach plant washers is the problem of monitoring the effectiveness of the protection of the stainless steel drum.

SUMMARY OF THE INVENTION (i) Aims of the Invention

Accordingly, one object of this invention is to provide a method for the effective electrochemical corrosion protection of stainless steel subjected to the action of a corrosive, oxidizing, chloride-containing liquor in which the effectiveness of the protection is monitored.

Another object of this invention is the provision of an assembly to monitor crevice corrosion in an electrochemically protected stainless steel drum.

(ii) Statement of the Invention

The present invention is embodied in a monitor assembly for monitoring the effectiveness of electrochemical crevice corrosion protection of a stainless steel member, comprising: (a) a mount adapted to be electrically connectable to the stainless steel member, the mount being adapted to be rigidly and fixedly secured to the stainless steel member, the mount having a threaded exposed end; (b) an electrically non-conductive sleeve disposed on the mount, the sleeve serving to isolate the mount electrically; (c) a first frusto-conical centrally apertured metal spacer disposed on the sleeve, in electrical contact with the mount; (d) a first stainless steel centrally apertured monitor coupon disposed on the sleeve in electrical contact with the first frusto-conical metal spacer; (e) a first segmented electrically non-conductive centrally apertured disc disposed on the sleeve in non-electrical contact with the first monitor coupon; (f) a second frusto-conical centrally apertured metal spacer, identical with the first frusto-conical metal spacer, disposed in non-electrical contact with the first segmented disc; (g) a second stainless steel centrally apertured monitor coupon identical to the first stainless steel monitor coupon, disposed on the sleeve, in contact with the second frusto-conical metal spacer; (h) a second electrically non-conductive centrally apertured segmented disc, identical with the first segmented disc, disposed on the sleeve in non-electrical contact with the second stainless steel monitor coupon; and (i) centrally apertured locknut threaded onto the mount and holding the members on the sleeve under a predetermined, substantially constant mechanical stress; wherein, the metal mount and the metal spacers are formed of any metal with sufficient mechanical and chemical stability to withstand the corrosive environment and the mechanical stress; wherein the electrically non-conductive sleeve and segmented discs are formed of an electrically non-conductive material having sufficient mechanical and chemical stability to withstand the corrosive environment and the mechanical stress and wherein the face-to-face contact of the first coupon with the first spacer and the first segmented disc is identical to the face-to-face contact of the second coupon with the second spacer and the second segmented disc.

The present invention is also embodied by the combination of stainless steel bleach plant washer perforated or foraminous drum, and welded to one end face thereof adjacent to the circumferential wall, a monitor assembly comprising: (a) a mount adapted to be electrically connectable to the stainless steel member, the mount being rigidly and fixedly secured to the end face of the stainless steel drum, the mount having a threaded exposed end; (b) an electrically non-conductive sleeve disposed on the mount, the sleeve serving to isolate the mount electrically; (c) a first frusto-conical centrally apertured metal spacer disposed on the sleeve, in electrical contact with the mount; (d) a first stainless steel centrally apertured monitor coupon disposed on the sleeve in electrical contact with the first frusto-conical metal spacer; (e) a first segmented electrically non-conductive centrally apertured disc disposed on the sleeve in non-electrical contact with the first monitor coupon; (f) a second frusto-conical centrally apertured metal spacer, identical with the first frusto-conical metal spacer, disposed on the sleeve in non-electrical contact with the first segmented disc; (g) a second stainless steel centrally apertured monitor coupon identical to the first stainless steel monitor coupon, disposed on the sleeve in contact with the second frusto-conical metal spacer; (h) a second electrically non-conductive centrally apertured segmented disc, identical with the first segmented disc, disposed on the sleeve in non-electrical contact with the second stainless steel monitor coupon; and (i) a centrally apertured locknut threaded onto the mount and holding the members on the sleeve under a predetermined, substantially constant, mechanical stress; wherein, the metal mount and the metal spacers are formed of any metal with sufficient mechanical and chemical stability to withstand the corrosive environment and the mechanical stress; wherein the electrically non-conductive sleeve and segmented discs are formed of an electrically non-conductive material having sufficient mechanical and chemical stability to withstand the corrosive environment and the mechanical stress; and wherein the face-to-face contact of the first coupon with the first spacer and the first segmented disc is identical to the face-to-face contact of the second coupon with the second spacer and the second segmented disc.

(iii) Other Features of this Invention

In one embodiment of this invention, the mount means may include a head and a threaded shank, in which the head is welded to the stainless steel member; or the mount means may include a head, a threaded shank, and a threaded extension from the head, and in which the threaded extension is threaded onto a tapped hole in the stainless steel member, or, alternatively onto a separate probe assembly which is electrically connected to the stainless steel member.

Preferred materials out of which either or both of the mount means or the frusto-conical spacers may be formed are the same stainless steel as the stainless steel member, or of a nickel-based alloy known by the Trade Mark of HASTELLOY C-276.

The sleeve is preferably formed of glass-filled polytetrafluoroethylene. The segmented discs and the locknut are preferably formed of a filled tetrafluoroethylene resin, or most perferably of such a resin known by the Trade Mark of RULON A.

The stainless steel coupons are preferably formed of the same stainless steel as the stainless steel member, and may be either substantially rectangular or substantially circular in shape.

The lock washer is preferably tightened to a 10 in-lb torque, and the segmented discs preferably have 20 grooves and plateaus on one face thereof.

BRIEF DESCRIPTION OF THE DRAWINGS

In the accompanying drawings,

FIG. 1 is an exploded elevational view of the components of the monitor of an aspect of this invention;

FIG. 2 is an elevational view of an alternative mount which may be used in the monitor shown in FIG. 1;

FIG. 3 is an elevational view of a partially assembled monitor; and

FIG. 4 is an elevational view of an assembled monitor.

DESCRIPTION OF PREFERRED EMBODIMENTS (i) Detailed Description of FIGS. 1, 3 and 4

As seen in FIGS. 1 and 4, the monitor 10 includes a mount 11 having an exposed threaded end 12. The mount 11 in FIG. 1 is shown welded to the end face of a stainless steel bleach plant washer drum 100. The mount 11 may be made of any metal which has sufficient mechanical and chemical stability to withstand the corrosive environment and to withstand mechanical stress, and which can be electrically and mechanically connected to the protected equipment. It may be a stainless steel, e.g., the same as that of the drum 100, but preferably it is HASTELLOY C-276, the Trade Mark of a nickel-based alloy of Cabot Corporation.

As shown more fully also in FIG. 3, a non-electrically conducting sleeve 15 is disposed on the mount 11. While the sleeve may be any electrically non-conducting material having sufficient mechanical and chemical stability to withstand the corrosive environment and the mechanical stress, it preferably is glass-filled TEFLON (the Trade Mark for polytetrafluoroethylene of DuPont).

A first frusto-conical centrally apertured metal spacer 16 is disposed on the sleeve 15 to be in electrical contact with mount 11. The larger diameter end of the spacer 16 is disposed in such contact with the mount 11. The spacer 16 may be made of any metal having sufficient mechanical and chemical stability to withstand the corrosive environment and the mechanical stress, and can be electrically and mechanically connected to the protected equipment. It may be a stainless steel, e.g., the same as that of the drum 100, but preferably it is HASTELLOY C-276.

A first stainless steel centrally apertured monitor coupon 17 is disposed on the sleeve 15 to be in electrical contact with the smaller diameter end of the spacer 16. The monitor coupon 17 is preferably made of the same stainless steel as the washer drum 100.

A first segmented centrally apertured disc 18 is disposed on the sleeve 15 to be in non-electrical contact with the first monitor coupon 17. The disc 18 may be any electrically non-conducting material having sufficient mechanical and chemical stability to withstand the corrosive environment and the mechanical stress, but is preferably a filled tetrafluoroethylene resin, e.g., that known by the Trade Mark RULON A of DuPont. The disc 18 preferably has twenty grooves and plateaus 18a and 18b respectively in contact with the monitor coupon 17, to provide twenty crevices per monitor coupon 17. The creviced/exposed surface area ratio should be at least 1:10 to assure sufficient cathode area substantially to prevent interference between crevices. The use of such segmented disc 18 is disclosed by D. B. Anderson, in a paper entitled "Statistical Aspects of Crevice Corrosion in Seawater" published in "Galvanic and Pitting Corrosion", Special Technical Publication 576, American Society for Testing & Materials; Editors: Baboain, France, Rowe, & Rynewicz, (1976) LCCCN #75-2510.

A second identical and identically disposed set of spacer 16', monitor coupon 17' and segmented disc 18' is disposed on the sleeve 15, but the monitor coupon 17' is electrically isolated from the mount 11.

Finally, the components are held together on the sleeve 15 by means of a non-electrically conductive centrally apertured lock washer 19. Lock washer 19 may be any material having sufficient mechanical and chemical stability to withstand the corrosive environment and the mechanical stress, but is preferably the resin known by the Trade Mark of RULON A of DuPont. The locknut is tightened to a torque of 10 in-lb.

In this way, the first monitor coupon 17 is in electrical contact with the drum 100 and the second monitor coupon 17' is in non-electrical contact with the drum 100. Both the first monitor coupon 17 and the second monitor coupon 17' are in identical face-to-face contact with their respective spacer (16 or 16') and segmented disc (18 or 18'). The contact pressure is also identical, e.g., 10 in-lb. Consequently, all variables except for the electrochemical protection have been eliminated for the monitor coupons 17 and 17'.

(ii) Detailed Description of FIG. 2

As shown in FIG. 2, the mount 11 is shown having a threaded extension 13 which is secured in a tapped hole 14 in the drum 100. While not shown, the mount 11 may alternatively be threaded onto a separate probe assembly which is electrically connected to the stainless steel member. The auxiliary components of the mount 11, e.g., the threaded extension 13, or the separate probe assembly, are formed out of the same material as described hereinabove for the mount 11.

(iii) Operation of the Preferred Embodiment

The effectiveness of the electrochemical corrosion protection of a bleach plant washer was confirmed using the monitor assembly described herein.

A monitor assembly mount was welded to one end face of a 317L stainless steel chlorine dioxide-stage bleach plant washer drum. A pair of 317L stainless steel coupons was then mounted as herein described, so that one coupon was electrically connected to the drum, which itself was electrochemically protected, and the other coupon was electrically isolated and thus not protected. In this way, ten coupons, each with identical surface finish were exposed in pairs for periods of between 28 and 62 days to the bleach pulp washer liquor, which contained up to 200 ppm $ClO_2$ and approximately 1000 ppm $Cl^-$, at a pH of 3.75 to 5 and temperatures in the range 55° to 65° C. The end face mounting of the assembly was such that coupons were given alternate wet-dry exposure as the drum rotated. After each exposure period, the coupons were removed and assessed by measuring the loss of weight which had resulted from exposure to the corrosion environment. The weight loss was area and time averaged to give corrosion rates, and the results are shown in Table I below:

TABLE I

| # | Exposure Period Time (days) | Type of Exposure | Corrosion Rate (mg.cm.$^{-2}$y$^{-1}$) |
|---|---|---|---|
| 1 | 28 | Not Protected | 0.84 |
|   |    | Protected | 0.24 |
| 2 | 62 | Not Protected | 0.70 |
|   |    | Protected | 0.35 |
| 3 | 25 | Not Protected | 1.15 |
|   |    | Protected | 0.19 |
| 4 | 31 | Not Protected | 1.02 |
|   |    | Protected | 0.62 |
| 5 | 31 | Not Protected | 0.65 |
|   |    | Protected | 0.12 |

Thus it can be seen, by comparing the weight loss of protected and unprotected coupons, that the electrochemical corrosion protection of this stainless steel chlorine dioxide-stage bleached pulp washer was indeed effective.

SUMMARY

From the foregoing description, one skilled in the art can easily ascertain the essential characteristics of this invention; and without departing from the spirit and scope thereof, can make various changes and modifications of the invention to adapt it to various usages and conditions. Consequently, such changes and modifications are properly, equitably, and "intended" to be, within the full range of equivalence of the following claims.

I claim:

1. A monitor assembly for monitoring the effectiveness of cathodic crevice corrosion protection of a stainless steel member, comprising:
   (a) a mount adapted to be electrically connectable to said stainless steel member, said mount being adapted to be rigidly and fixedly secured to said stainless steel member, said mount having a threaded exposed end;

(b) an electrically non-conductive sleeve disposed on said mount, said sleeve serving to isolate the mount electrically;

(c) a first frusto-conical centrally apertured metal spacer disposed on said sleeve, in electrical contact with said mount;

(d) a first stainless steel centrally apertured monitor coupon disposed on said sleeve in electrical contact with said first frusto-conical metal spacer;

(e) a first segmented electrically non-conductive centrally apertured disc disposed on said sleeve in non-electrical contact with said first monitor coupon;

(f) a second frusto-conical centrally apertured metal spacer, identical with said first frusto-conical metal spacer, disposed in non-electrical contact with said first segmented disc;

(g) a second stainless steel centrally apertured monitor coupon identical to said first stainless steel monitor coupon, disposed on said sleeve, in contact with said second frusto-conical metal spacer;

(h) a second electrically non-conductive centrally apertured segmented disc, identical with said first segmented disc, disposed on said sleeve in non-electrical contact with said second stainless steel monitor coupon; and (i) a centrally apertured locknut threaded onto said mount and holding the members on said sleeve under a predetermined, substantially constant, mechanical stress;

wherein, said metal mount and said metal spacers are formed of any metal with sufficient mechanical and chemical stability to withstand the corrosive environment and the mechanical stress;

wherein, said electrically non-conductive sleeve and segmented discs are formed of an electrically non-conductive material having sufficient mechanical and chemical stability to withstand the corrosive environment and the mechanical stress;

and wherein, the face-to-face contact of said first coupon with said first spacer and said first segmented disc is identical to the face-to-face contact of said second coupon with said second spacer and said second segmented disc.

2. The monitor of claim 1 wherein said mount includes a head and a threaded shank, and said head is welded to said stainless steel member.

3. The monitor of claim 1 wherein said mount includes a head, a threaded shank, and a threaded extension from the head, and said threaded extension is threaded onto a tapped hole in said stainless steel member.

4. The monitor of claim 1 wherein said mount includes a head, a threaded shank, and a threaded extension from the head, and said threaded extension is threaded onto a tapped hole in said stainless steel member and said threaded extension is threaded onto a separate probe assembly which is electrically connected to said stainless steel member.

5. The monitor of claim 1 wherein said mount is formed of the same stainless steel as said stainless steel member.

6. The monitor of claim 1 wherein mount is formed of a nickel-based alloy known by the Trade Mark HASTELLOY C-276.

7. The monitor of claim 1 wherein said sleeve is formed of glass filled polytetrafluoroethylene.

8. The monitor of claim 1 wherein said frusto-conical spacers are formed of the same stainless steel as said stainless steel member.

9. The monitor of claim 1 wherein said frusto-conical spacers are formed of a nickel-based alloy known by the Trade Mark HASTELLOY C-276.

10. The monitor of claim 1 wherein said segmented discs and said locknut are formed of a filled tetrafluoroethylene resin.

11. The monitor of claim 10 wherein said resin is that known by the Trade Mark of RULON A.

12. The monitor of claim 1 wherein said stainless steel coupons are formed of the same stainless steel as said stainless steel member and are substantially rectangular.

13. The monitor of claim 1 wherein said stainless steel coupons are formed of the same stainless steel as said stainless steel member and are substantially circular.

14. The monitor of claim 1 wherein said lock washer is tightened to a 10 in-lb torque.

15. The monitor of claim 1 wherein said segmented discs have 20 grooves and plateaus on a face thereof.

16. In combination, a stainless steel bleach plant washer perforated or foraminous drum, and welded to one end face thereof adjacent to the circumferential wall, a monitor assembly comprising:

(a) a mount adapted to be electrically connectable to said stainless steel member, said mount being rigidly and fixedly secured to said end face of said stainless steel drum, said mount having a threaded exposed end;

(b) an electrically non-conductive sleeve disposed on said mount, said sleeve serving to isolate the mount electrically;

(c) a first frusto-conical centrally apertured metal spacer disposed on said sleeve, in electrical contact with said mount;

(d) a first stainless steel centrally apertured monitor coupon disposed on said sleeve in electrical contact with said first frusto-conical metal spacer;

(e) a first segmented electrically non-conductive centrally apertured disc disposed on said sleeve in non-electrical contact with said first monitor coupon;

(f) a second frusto-conical centrally apertured metal spacer, identical with said first frusto-conical metal spacer, disposed on said sleeve in non-electrical contact with said first segmented disc;

(g) a second stainless steel centrally apertured monitor coupon identical to said first stainless steel monitor coupon, disposed on said sleeve in contact with said second frusto-conical metal spacer;

(h) a second electrically non-conductive centrally apertured segmented disc, identical with said first segmented disc, disposed on said sleeve in non-electrical contact with said second stainless steel monitor coupon; and (i) a centrally apertured locknut threaded onto said mount and holding the members on said sleeve under a predetermined, substantially constant, mechanical stress;

wherein, said metal mount and said metal spacers are formed of any metal with sufficient mechanical and chemical stability to withstand the corrosive environment and the mechanical stress, wherein, said electrically non-conductive sleeve and segmented discs are formed of an electrically non-conductive material having sufficient mechanical and chemical stability to withstand the corrosive environment and the mechanical stress; and wherein, the face-to-face contact of said first coupon with said first spacer and said first segmented disc is identical to the face-to-face contact of said second coupon with said second spacer and said second segmented disc.

* * * * *